United States Patent [19]

Sameshima et al.

[11] 3,975,411

[45] Aug. 17, 1976

[54] PROCESS FOR PREPARING 1-AMINOANTHRAQUINONE

[75] Inventors: Muneyasu Sameshima; Tagui Osawa; Utaka Hirai, all of Omuta, Japan

[73] Assignee: Mitsui Toatsu Chemicals, Incorporated, Tokyo, Japan

[22] Filed: Mar. 10, 1975

[21] Appl. No.: 557,058

[30] Foreign Application Priority Data

Sept. 9, 1974   Japan.............................. 49-104824

[52] U.S. Cl................................. 260/378; 260/369
[51] Int. Cl.$^2$.......................................... C07C 97/24
[58] Field of Search............................ 260/378, 369

[56]         References Cited
         UNITED STATES PATENTS 2,948,739   8/1960   Harris et al. ....................... 260/369

FOREIGN PATENTS OR APPLICATIONS 2,200,071   1972   Germany
2,340,114   1973   Germany

OTHER PUBLICATIONS

Vorozhtsou et al. Chemical Abstracts, 55 (1961) Column 1547 e–g.

*Primary Examiner*—Arthur P. Demers
*Attorney, Agent, or Firm*—Fisher, Christen & Sabol

[57]         ABSTRACT

5-Nitro-1,4,4a,9a-tetrahydroanthraquinone is suspended in water in the form of a powder and then catalytically hydrogenated in the presence both of a hydrogenation catalyst containing a metal such as palladium, platinum or the like as its effective component and of a base such as sodium hydroxide, pyridine or the like thereby to form a hydroquinone type compound of 1-aminoanthraquinone. By contacting the resultant reaction solution with air or by adding an oxidizing agent such as hydrogen peroxide to the reaction solution, the hydroquinone type compound is readily oxidized into 1-aminoanthraquinone in the suspended state.

15 Claims, No Drawings

PROCESS FOR PREPARING 1-AMINOANTHRAQUINONE

BACKGROUND OF THE INVENTION

1. Field of the Invention

This invention relates to a novel process for the preparation of 1-aminoanthraquinone using as starting material 5-nitro-1,4,4a,9a-tetrahydroanthraquinone (hereinafter referred to simply as 5-nitrotetrahydroanthraquinone) expressed by the formula:

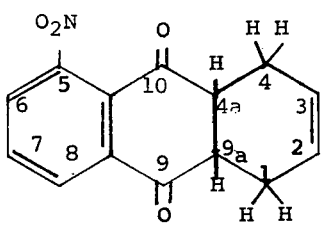

2. Description of the Prior Art

1-Aminoanthraquinone is important as an intermediate for anthraquinone-base disperse dyes, vat dyes and pigments, and has been heretofore synthesized through anthraquinone-1-sulfonic acid obtained by the sulfonation of anthraquinone. However, this prior art process is difficult to practice since it involves the use of a mercury catalyst in the sulfonation step, thus presenting many problems concerning the work environment and environmental pollution. Various methods for the preparation of 1-aminoanthraquinone as alternatives to the above process have been investigated, among which a method of preparation using nitration and reduction reactions of anthraquinone has been assumed to be most effective. However, this method using the nitration and reduction of anthraquinone involves the use of large amounts of sulfuric acid and nitric acid, offering problems in handling of the acids and in treatment of the resultant waste liquor. Additionally, 1-aminoanthraquinone obtained by this method contains a large quantity of by-products including diamino compounds and the 2-amino compound, and must essentially be purified by complicated operations for use as an intermediate of dye. Thus, this method is not successful from the industrial point of view.

There have also been proposed several process for the preparation of 1-nitroanthraquinone wherein 5-nitro-1,4-naphthoquinone (hereinafter referred to simply as 5-nitronaphthoquinone) is condensed with 1,3-butadiene to give 5-nitrotetrahydroanthraquinone, followed by oxidation to obtain 1-nitroanthraquinone. For example, according to N. N. Woroshtzov et al. (Khim. Nauka i Prom, 5, 474 – 475, 1960), 1-nitroanthraquinone can be obtained by condensing 5-nitronaphthoquinone and 1,3-butadiene in ethanol and oxidizing the resultant condensation product with air in an alcoholic alkali solution. Moreover, French Pat. No. 1,486,803 (Institut Premyslu Organiznco) describes a process for the preparation of 1-nitroanthraquinone by reacting butadiene with 5-nitronaphthoquinone in nitrobenzene and oxidizing the resultant reaction product by means of nitrobenzene in the presence or absence of piperidine without isolation of the reaction product. 1-Nitroanthraquinone obtained by these processes can be readily converted into 1-aminoanthraquinone by an ordinary reduction method. However, these processes have a vital disadvantage in that when 5-nitrotetrahydroanthraquinone which is obtained by condensation of 5-nitronaphthoquinone and 1,3-butadiene is dissolved in a suitable solvent after isolation thereof, or as it is without isolation, and then air is fed into the solution for oxidation in the presence of a base such as piperidine, various by-products are also produced, so that 1-aminoanthraquinone obtained by reduction of the resultant 1-nitronaphthoquinone with the various by-products is low in purity. As a result, it is difficult to use such 1-aminoanthraquinone as an intermediate for dyes.

SUMMARY OF THE INVENTION

It is a primary object of the present invention to provide a novel process for preparing 1-aminoanthraquinone from starting 5-nitrotetrahydroanthraquinone.

It is another object of the present invention to provide a process for preparing, from 5-nitrotetrahydroanthraquinone, 1-aminoanthraquinone of high purity which can be used, as it is, as an intermediate for dyes or other substances.

The above objects can be achieved by suspending 5-nitrotetrahydroanthraquinone in an aqueous reaction medium, catalytically hydrogenating the 5-nitrocompound in the presence of a hydrogenation catalyst and a base, and oxidizing the resultant over-reduced compound into 1-aminoanthraquinone by air or an oxidizing agent.

Upon completion of the reaction, 1-aminoanthraquinone is suspended in the reaction medium together with the catalyst. Accordingly, 1-aminoanthraquinone as well as the catalyst can be separated from the reaction medium by filtration. To the resultant cake is added a solvent capable of dissolving 1-aminoanthraquinone alone for separating the catalyst and to obtain a solution of 1-aminoanthraquinone. In this connection, as will be described in detail hereinafter, when a hydroxide of an alkali metal or an alkaline earth metal is employed as a base in an amount of greater than $2/n$ mols (wherein $n$ is the valence of the metal) per mol of 5-nitrotetrahydroanthraquinone, the over-reduced compound is obtained in a dissolved state in the reaction solution upon completion of the catalytic hydrogenation reaction, from which the catalyst alone can be easily removed by filtration. By subjecting the thus obtained catalyst-free solution to oxidation, 1-aminoanthraquinone can be obtained in a suspended state.

Though the reaction mechanism occurring in the process of the present invention cannot be clearly defined at the present stage of investigation, it is assumed that the hydrogenation in the presence of a base causes reduction of the nitro group into an amino group and, at the same time, dehydrogenation of the tetrahydro ring. The over-reduced compound obtained as an intermediate in the process of the present invention is considered to be a hydroquinone type compound of 1-aminoanthraquinone having the following formula:

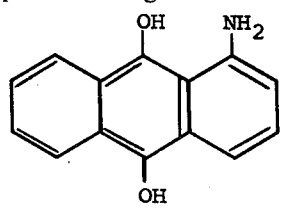

In accordance with the present invention, there are secondarily produced no diamino compounds which would be always produced in the prior art processes involving nitration of anthraquinone, so that highly pure 1-aminoanthraquinone can be obtained without special purification.

DESCRIPTION OF THE PREFERRED EMBODIMENTS

The 5-nitrotetrahydroanthraquinone used as starting material in the process of the present invention is prepared by a Diels-Alder condensation of 5-nitronaphthoquinone and 1,3-butadiene. 5-Nitronaphthoquinone can be obtained with ease, for example, by nitration of 1,4-naphthoquinone by nitric acid in sulfuric acid. Even though the starting 5-nitro compound may contain a small amount of impurities such as 6-nitrotetrahydroanthraquinone, no influence will be exerted thereby on the reaction process of the present invention.

The aqueous reaction medium useful in the present invention can be water per se or a mixed solution of water and an organic solvent miscible with water. Examples of such organic solvents include alcohols such as methanol, ethanol, propanol, ethylene glycol, propylene glycol, glycerine and the like, ethers such as dioxane, 1,2-dimethoxyethane, 1,2-diethoxyethane and the like, and ether alcohols such as diethylene glycol, dipropylene glycol and the like. Even when these organic solvents are not used for mixing with water and water alone is used as the reaction medium, the purpose of the present invention can be fully attained. When used, the organic solvent can be mixed with water in an amount up to 50% by weight or in a weight ratio up to 1:1.

The amount of the aqueous reaction medium is generally 5 to 100 times by weight, preferably 10 to 50 times by weight, as great as that of the starting 5-nitrotetrahydroanthraquinone. With an amount less than 5 times by weight, the reaction will sometimes proceed incompletely since it is difficult to satisfactorily agitate the suspended 5-nitrotetrahydroanthraquinone due to the small amount of the reaction medium.

Hydrogenation catalysts suitable for the practice of the present invention are those which are ordinarily used for catalytic hydrogenation of a nitro compound into a corresponding amino compound. For example, a catalyst which contains as its effective component palladium, platinum, ruthenium, rhodium, nickel, cobalt, copper and/or the like metal, or a copper-chromium catalyst is suitable for this purpose. Especially, a platinum group catalyst supported on a carrier such as of carbon, alumina, diatomaceous earth or the like or a Raney nickel catalyst is most suitable in the present invention. The catalyst is used in a catalytically effective amount and the amount of catalyst will vary depending upon the reaction conditions and the kind of catalyst. When a platinum group catalyst supported on a carrier is used, the amount is preferably in the range of from 0.002 to 0.5 parts by weight (in terms of the platinum group metal) per 100 parts of the starting 5-nitrotetrahydroanthraquinone. When a platinum group catalyst such as palladium black is used without a carrier, the amount is preferably in the range of from 0.01 to 5 parts by weight per 100 parts of 5-nitrotetrahydroanthraquinone. Furthermore, with a nickel, cobalt, copper or copper-chromium catalyst, the amount is preferably in the range of from 0.05 to 20 parts by weight per 100 parts of 5-nitrotetrahydroanthraquinone.

Although substantially all ordinary basic substances are employable as the base useful in the process of the present invention, there are generally suitably used hydroxides, carbonates, acetates and phosphates of metals such as sodium, potassium, calcium, barium, magnesium and the like, ammonia, diethylamine, morpholine, piperidine, ethanolamine triethanolamine, piperazine and the like. The amount of the base used is generally greater than 1 mol, preferably from 1 to 20 mols, per mol of 5-nitrotetrahydroanthraquinone. The above-mentioned bases may be used singly or in combination.

The hydrogenation of the present invention is operable at normal atmospheric pressure or under elevated pressure. That is, the present invention may be practiced by an atmospheric pressure process wherein 5-nitrotetrahydroanthraquinone, aqueous reaction medium, base and catalyst are placed in a reactor equipped with an agitator and a hydrogen inlet for the hydrogenation reaction, into which reactor is fed hydrogen while agitating the reaction mixture, at a predetermined temperature. The present invention may also be practiced by an elevated pressure process wherein the above-mentioned starting materials are placed in an autoclave into which hydrogen is fed under pressure with agitating or shaking. The hydrogen may be fed into the autoclave at a pressure of from 0.5 to 100 kg/cm$^2$ and the reaction may be carried out at a pressure up to 100 kg/cm$^2$.

The reaction temperature may be in a wide range of 0° to 160°C. since little or no potential side reactions take place in the hydrogenation of the present invention. For convenience of reaction operation, the temperature is preferably within the range of 10° to 120°C.

In order to facilitate the reaction, there may be used a surface active agent which does not adversely affect the hydrogenation reaction. For example, a nonionic active agent such as a polyoxyethylene alkyl ether, a polyoxyethylene alkyl aryl ether, a polyoxyethylene alkyl ester or a polyoxyethylenesorbitan monoalkyl ester, or an anionic active agent of the alkyl aryl sulfonate type is effective for this purpose and the amount thereof is generally from 0.001 to 1.0 parts by weight, preferably from 0.005 to 0.5 parts by weight per part of 5-nitrotetrahydroanthraquinone. Addition of the surface active agent to the reaction system favorably affects the reaction system, i.e., the physical properties at the interface between the reaction medium and the suspended material change so that the reaction proceeds easily even at a high slurry concentration, agitation of the reaction mixture is facilitated and the reaction rate is increased to some degree.

The hydrogenation reaction is effected under the aforementioned reaction conditions whereby from 1.1 to 2.2 mols of hydrogen is absorbed in 1 mol of 5-nitrotetrahydroanthraquinone. After completion of the hydrogenation, the resultant solution is subjected to oxidation at a temperature of from 0° to 150°C. with use of air or an oxidizing agent such as hydrogen peroxide. The air or other oxidizing agent should be used in an amount required and sufficient to oxidize the over-reduced compound in the reaction solution into 1- aminoanthraquinone. Other oxidizing agents which may be used include perbenzoic acid, tert-butyl peroxide, sodium peroxide, potassium dichromate, and the like.

The solvent which is capable of dissolving 1-aminoanthraquinone alone and which is used for separating the catalyst from the reaction product may be, for example, an aliphatic glycol such as ethylene glycol, propylene glycol, diethylene glycol or the like, an alicyclic alcohol such as cyclohexanol, methylcyclohexanol or the like, a carboxylic acid amide such as N,N-dimethylforamide, N,N-dimethylacetamide, N-methyl-2-pyrrolidone or the like, an ether such as dioxane, tetrahydrofuran, methoxybenzene or the like, an alkylbenzene such as toluene, xylene or the like, a halogenated benzene such as chlorobenzene, dichlorobenzene or the like, an ether alcohol such as methoxyethanol or the like, dimethyl sulfoxide or sulfuric acid. The solution of the reaction product from which the catalyst is removed is cooled or diluted with a non-solvent for 1-aminoanthraquinone such as water, or is subjected to concentration whereby 1-aminoanthraquinone can be obtained efficiently.

When the hydrogenation reaction is effected using as a base a hydroxide of an alkali metal or an alkaline earth metal, including sodium hydroxide or potassium hydroxide, in an amount of $2/n$ mol (wherein $n$ is the valence of the metal of the base) per mol of 5-nitrotetrahydroanthraquinone, the resultant product is obtained in the form of an alkali metal salt or an alkaline earth metal salt of the hydroquinone type compound of 1-aminoanthraquinone which is soluble in the reaction solution, so that the catalyst can be separated by filtration without use of the aforementioned organic solvent. In this case, highly pure 1-aminoanthraquinone can be efficiently obtained by oxidizing the catalyst-free solution by means of air or an oxidizing agent such as hydrogen peroxide at a predetermined temperature of from 0° to 150°C. The thus obtained 1-aminoanthraquinone contains substantially no side products and may be accordingly employed, as it is, as an intermediate for a dye or pigment.

The present invention will be particularly illustrated by the following examples wherein all parts are parts by weight unless otherwise specified. Purity of the products was determined by an infrared absorption spectrum analysis in all examples.

EXAMPLE 1

2.6 Grams (0.01 mol) of 5-nitrotetrahydroanthraquinone, 52 grams (0.013 mol) of a 1% aqueous sodium hydroxide solution, and 0.052 grams of a 5% palladium on carbon catalyst were introduced into an electromagnetic agitation-type glass reactor having an inner volume of 200 ml. Then, the atmosphere in the reactor was replaced by hydrogen, followed by hydrogenation while agitating at room temperature. When 0.015 mol of hydrogen was absorbed, the hydrogen in the system was replaced by nitrogen and then by air for oxidizing the resultant over-reduced compound while agitating for 30 minutes. The resultant reaction product was separated together with the catalyst by filtration and was dissolved in N,N-dimethylformamide for separating the catalyst by filtration. To the resultant filtrate was added water for dilution to obtain 2.1 grams of 1-aminoanthraquinone (at a yield of 93.1%). The purity of the 1-aminoanthraquinone was 98%.

EXAMPLE 2

The process of Example 1 was repeated using sulfuric acid instead of N,N-dimethylformamide for separation of the catalyst. Similar results were obtained.

EXAMPLE 3

The same amounts of 5-nitrotetrahydroanthraquinone, aqueous sodium hydroxide solution and palladium on carbon catalyst as in Example 1 were placed in a cylindrical glass reactor having an inner volume of 500 ml and equipped with a thermometer, an agitator, a hydrogen inlet and a reflux condenser, into which was fed hydrogen at a flow rate of 1 l/min for hydrogenation while agitating the reaction mixture at room temperature for 6 hours. Thereafter, air for oxidation was fed into the reaction system at a flow rate of 1 l/min for 30 minutes. The resultant reaction product containing therein the catalyst was separated by filtration, followed by dissolution thereof in methyl cellosolve (i.e., $\beta$-hydroxyethyl methyl ether) for separating therefrom the catalyst. The resultant filtrate was condensed to obtain 2.1 grams of 1-aminoanthraquinone (at a yield of 93.1%). The purity of the 1-aminoanthraquinone was 98%.

EXAMPLE 4

2.6 Grams (0.01 mol) of 5-nitrotetrahydroanthraquinone, 52 grams (0.032 mol) of a 2.5% aqueous sodium hydroxide solution and 0.07 gram of a Raney nickel catalyst were placed in an electromagnetic agitation-type autocalve with an inner volume of 160 ml, followed by hydrogenation while agitating under a pressure of 3 to 6 kg/cm$^2$G at room temperature. The hydrogenation reaction proceeded smoothly. 6 Hours after commencement of the reaction, 0.02 mol of hydrogen was absorbed and the absorption was stopped. Then, the hydrogen in the reaction system was replaced by nitrogen and the resultant reaction solution was filtered in a flow of nitrogen for separating the catalyst therefrom. Air was passed into the resultant filtrate for oxidation to obtain 2.1 grams of 1-aminoanthraquinone (at a yield of 93.1%). The purity was 97%.

EXAMPLE 5

25.7 Grams (0.1 mol) of crude 5-nitrotetrahydroanthraquinone obtained by condensing in ethanol 1,3-butadiene and 5-nitro-1,4-naphthoquinone containing therein 10% of 6-nitro-1,4-naphthoquinone was placed in a reactor having an inner volume of 2 liters together with 514 grams (0.13 mol) of a 1% aqueous sodium hydroxide solution and 0.52 gram of a 5% palladium on carbon catalyst and was hydrogenated with hydrogen at room temperature and under normal pressure with agitation. The hydrogenation reaction was stopped when 0.2 mol of hydrogen was abosrbed. Into the resultant reaction solution was fed air for oxidizing the over-reduced compound formed. The resultant reaction product was separated by filtration together with the catalyst. The thus separated product was mixed with N,N-dimethylformamide for dissolving the product alone, followed by separation of the catalyst by filtration. The resultant filtrate was diluted with water for precipitation to obtain 21 grams of 1-aminoanthraquinone containing therein 2% of 2-aminoanthraquinone (at a yield of 94.2%).

EXAMPLE 6

The procedure of Example 1 was repeated with the exception that 52 grams of an aqueous solution which contained 0.87 grams (0.01 mol) of morpholine was used instead of the 1% sodium hydroxide aqueous solution. The resultant reaction product was separated by filtration from the reaction solution together with the catalyst. Then, the product was dissolved in N,N-dimethylformamide for separating the catalyst by filtration, to which was added water for dilution thereby to precipitate crystals. The thus precipitated crystals were separated by filtration, washed with water and dried to obtain 2.1 grams of 1-aminoanthraquinone (at a yield of 93.1%). The purity was 97%.

EXAMPLE 7

The procedure of Example 6 was repeated with the exception that the 52 grams of aqueous solution contained 1.49 grams (0.01 mol) of triethanolamine instead of the morpholine. Similar results were obtained.

EXAMPLE 8

The procedure of Example 6 was repeated with the exception that the 52 grams of aqueous solution contained 0.86 gram (0.01 mol) of piperazine instead of the morpholine. Similar results were obtained.

EXAMPLE 9

The hydrogenation reaction of Example 1 was repeated with the exception that the 1% sodium hydroxide aqueous solution was used in an amount of 120 grams (0.03 mol). The reaction was completed 3 hours after commencement of the reaction and 0.02 mol of hydrogen was absorbed. In this example, the resultant product was completely dissolved in the solution. The catalyst was separated by filtration in a flow of nitrogen. Then, air was passed into the resultant filtrate for oxidation to obtain 2.16 grams of 1-aminoanthraquinone (at a yield of 95.7%). The purity was 97%.

EXAMPLE 10

The procedure of Example 9 was repeated using 120 grams of an aqueous solution containing therein 0.024 mol of barium hydroxide instead of the 1% sodium hydroxide aqueous solution. Similar results were obtained.

EXAMPLE 11

The hydrogenation reaction of Example 9 was repeated with the exception that 0.5 gram of a polyoxyethylene nonyl phenyl ether (Emulgen 905 manufactured by Kao-Atlas Co., Ltd.) was also added to the reactor. The reaction was completed 2 hours after commencement of the reaction during which time 0.02 mol of hydrogen was absorbed and the resultant product was completely dissolved in the solution. The catalyst was separated by filtration in a flow of nitrogen. Then, air was passed into the resultant filtrate for oxidation to obtain 2.16 grams of 1-aminoanthraquinone (at a yield of 95.7%). The purity was 97%.

What is claimed:

1. A process for the preparation of 1-aminoanthraquinone comprising the steps of catalytically hydrogenating 5-nitro-1,4,4a,9a-tetrahydroanthraquinone in an aqueous reaction medium in the presence of a catalytically effective amount of a hydrogenation catalyst and a base and oxidizing the resultant reaction product with air or an oxidizing agent.

2. The process according to claim 1 wherein said aqueous reaction medium is water per se.

3. The process according to claim 1 wherein the hydrogenation reaction is carried out in the presence of a surface active agent.

4. The process according to claim 1 further comprising separating the reaction product from the reaction system together with said catalyst, dissolving said reaction product in an organic solvent and separating said catalyst from said reaction product.

5. The process according to claim 1 wherein the hydrogenation catalyst is used in an amount ranging from about 0.002 to about 20 parts by weight per 100 parts of 5-nitro-1,4,4a,9a-tetrahydroanthraquinone.

6. The process according to claim 1 wherein the hydrogenation is carried out at a temperature of from 0° to 160°C. and that a pressure between atmospheric pressure and an elevated pressure of up to 100 kg/cm$^2$.

7. The process accroding to claim 1 wherein the reaction is continued until from 1.1 to 2.2 mols of hydrogen is absorbed in each one mol of 5-nitro-1,4,4a,9a-tetrahydroanthraquinone.

8. The process according to claim 1 wherein said base is the hydroxide of an alkali metal or an alkaline earth metal and said hydroxide is used in an amount of at least $2/n$ mols per mol of said 5-nitro-1,4,4a,9a-tetrahydroanthraquinone, $n$ representing the valence of the metal of said base.

9. The process according to claim 8 which further comprises removing the hydrogenation catalyst from the reaction solution prior to oxidizing the resultant filtrate with air or an oxidizing agent.

10. The process according to claim 9 wherein said hydrogenation catalyst is palladium supported on a carbon carrier and the oxidation reaction is carried out with air.

11. The process according to claim 1 wherein the aqueous reaction medium is a mixture of water with up to 50% by weight of an organic solvent miscible with water.

12. The process according to claim 1 wherein the aqueous reaction medium is present in an amount of at least 5 parts by weight per part of the starting 5-nitro-1,4,4a,9a-tetrahydroanthraquinone.

13. The process according to claim 1 wherein the base is used in an amount of at least 1 mol per mol of 5-nitro-1,4,4a,9a-tetrahydroanthraquinone.

14. The process according to claim 1 wherein the reaction product is oxidized at a temperature of 0° to 150°C.

15. The process according to claim 3 wherein the surface active agent is used in an amount of from 0.001 to 1.0 parts by weight per part of 5-nitro-1,4,4a,9a-tetrahydroanthraquinone.

* * * * *